United States Patent [19]

Oehrlein et al.

[11] Patent Number: 5,888,777
[45] Date of Patent: Mar. 30, 1999

[54] PROCESS FOR THE COMPLETE REMOVAL OF PROTECTIVE GROUPS ON NUCLEOSIDE DIPHOSPHATE AND TRIPHOSPHATE SUGARS WITH ACETYLESTERASE

[75] Inventors: Reinhold Oehrlein, Rheinfelden; Gabriele Baisch, Binzen, both of Germany

[73] Assignee: Novartis AG, Basel, Switzerland

[21] Appl. No.: 875,882

[22] PCT Filed: Feb. 1, 1996

[86] PCT No.: PCT/EP96/00422

§ 371 Date: Aug. 6, 1997

§ 102(e) Date: Aug. 6, 1997

[87] PCT Pub. No.: WO96/24683

PCT Pub. Date: Aug. 15, 1996

[30] Foreign Application Priority Data

Feb. 7, 1995 [CH] Switzerland ............................... 363/95

[51] Int. Cl.$^6$ .............................. C12P 19/30; C12P 19/38
[52] U.S. Cl. ................................................ 435/89; 435/87
[58] Field of Search ........................................ 435/87, 89

[56] References Cited

PUBLICATIONS

Sachdev et al. (1969) Tetrahedron Lett., 9, "Enzymic Removal of Acyl Protecting Groups. Use of Dihydrocinnamoyl Group in Oligonucleotide Synthesis and its Cleavage by α–Chymotrypsin", pp. 733–736, in Chem. Abst. (1969) 70, p. 33, Abstract No. 111842r.

Taunton–Rigby (1973) J. Org. Chem. 38(5), "Oligonucleotide Synthesis, III: Enzymically Removable Acyl Protecting Groups", pp. 977–985.

Uemura et al. (1989) Tetrahedron Lett., 30(29), "Regioselective Deprotection of 3',5'–O–Acylated Pyrimidine Nucleosides by Lipase and Esterase", pp. 3819–3820.

Singh et al. (1993) Tetrahedron Lett., 34(33), "Enzymatic Regioselective Deacylation of 2',3',5'–Tri–O–Acylribonucleosides: Enzymatic Synthesis of 2',3'–Di–O–Acylribonucleosides", pp. 5201–5204.

Damjær et al. (1994) Nucleosides and Nucleotides, 13(8), "Lipase Catalyzed Diastereoselective Deacetylations of Anomeric Mixtures of Peracetylated 2'–Deoxynucleosides", pp. 1801–1807.

Taylor–Papadimitriou et al., Bock, K., et al., (Eds.), "Aberrant glycosylation of the MUCI gene product in adenocarcinomas: Implications for immunotherapy" in Complex Carbohydrates in Drug Research, Alfred Benzon Symposium 36, Munksgaard, Copenhagen 382–393 (1994).

Samuelsson et al., Bock, K., et al., (Eds.) "Carbohydrate antigents as targets for human allo–and xeno–antibodies: Pig–to–primate xenotransplantation" in Complex Carbohydrates in Drug Research, Alfred Benzon Symposium 36, Munksgaard, Copenhagen 368–397 (1994).

Karl–Anders et al., Bock, K., et al., (Eds.), "Carbohydrate attachment sites for microbes on animal cells: Aspects on the possible use of analogs to treat infections" in Complex Carbohydrates in Drug Research, Alfred Benzon Symposium 36, Munksgaard, Copenhagen 397–409 (1994).

Bock, K., et al., (Eds.), "Discussion" in Complex Carbohydrates in Drug Research, Alfred Benzon Symposium 36, Munksgaard, Copenhagen 366–367 (1994).

Hart et al., Bock, K., et al., (Eds.), "Nuclear and cytoplasmic glycosylation is ubiquitous and has the hallmarks of a regulatory modification" in Complex Carbohydrates in Drug Research, Alfred Benzon Symposium 36, Munksgaard, Copenhagen 280–290 (1994).

Kobata, Bock, K., et al., (Eds.), "Problems in producing glycoprotein drugs by gene technology and their use for the study of the functional roles of sugar chains" in complex Carbohydrates in Drug Research, Alfred Benzon Symposium 36, Munksgaard, Copenhagen 246–256 (1994).

Hansen et al., Bock, K., et al., (Eds.), "Role of carbohydrate on HIV and possibilites for anti–viral intervention" in Complex Carbohydrates in Drug Research, Alfred Benzon Symposium 36, Munksgaard, Copenhagen 414–427 (1994).

Hakomori, Bock, K., et al., (Eds.), "Role of carbohydrates in cell adhesion and recognition" in Complex Carbohydrates in Drug Research, Alfred Benzon Symposium 36, Munksgaard, Copenhagen 337–349 (1994).

Calusen et al., Bock, K., et al., (Eds.), "Simple mucin type O–glycans of HIV: Enzymatic prediction of glycosylation sites for vaccine construction" in Complex Carbohydrates in Drug Research, Alfred Benzon Symposium 36, Munksgaard, Copenhagen 297–310 (1994).

Meldal et al., Bock, K., et al., (Eds.), "Synthesis and biological application of glycosylated peptide templates" in Complex Carbohydrates in Drug Research, Alfred Benzon Symposium 36, Munksgaard, Copenhagen 153–164 (1994).

Ichikawa et al., Bock, K., et al., (Eds.), "Topochemistry and inhibition of selectin–mediated cell adhesion: Chemical–enzymatic synthesis of inhibitors related to E–selectin recognition" in Complex Carbohydrates in Drug Research, Alfred Benzon Symposium 36, Munksgaard, Copenhagen 118–130 (1994).

Gokhale, U.B., Hindsgaul, O., Palcic, M.M., Can. J. Chem 68:1063–1071 (1990).

Hakomori, S., Cancer Res. 45:2405–2414 (1985).

Heidlas, J.E., et al., J. Org. Chem. 57:146–151 (1992).

Ichikawa, Y., et al., Anal. Biochem. 202:215–238 (1992).

(List continued on next page.)

*Primary Examiner*—Jon P. Weber
*Attorney, Agent, or Firm*—Gregory D. Ferraro

[57] ABSTRACT

A process for the preparation of nucleoside diphosphate and triphosphate sugars wherein hydroxyl protective groups are removed enzymatically, with acetylesterase and a process for the preparation of these sugars, which comprises coupling a nucleotide with a sugar-1-phosphate activated with a carbonyl bisazole and then removing the hydroxyl protective groups enzymatically with acetylesterase.

25 Claims, No Drawings

OTHER PUBLICATIONS

Ichikawa, Y., et al., J. Org. Chem. 57:2943–2946 (1992).

Kennedy, J.F., et al., Carbohydrate Chemistry, Clarendon Press, Oxford 3–41 (1988).

Lehninger, A.L., Biochemistry, 298–321 (1993).

Leon, B., et al., Synthesis 698–691 (1994).

Nuñez, H.A., et al., Can. J. Chem. 59:2086–1095 (1981).

Seyfried, T.N., Developmental Biology 123:286–291 (1987).

Stiller, R., et al., Liebigs Ann Chem 467–471 (1992).

Thomas, R.L., et al., Carbohydr. Res. 184:77–85 (1988).

Waldmann, H., et al., Chem. Rev. 94:911–937 (1984).

Yamamoto, K., et al., Agric. Biol. Chem. 48:823–824 (1984).

Yamazaki, T., et al., Can. J. Chem. 59:2247–2252 (1981).

Yamazaki, T., et al., Carbohydr. Res. 79:C9–C12 (1980).

PROCESS FOR THE COMPLETE REMOVAL OF PROTECTIVE GROUPS ON NUCLEOSIDE DIPHOSPHATE AND TRIPHOSPHATE SUGARS WITH ACETYLESTERASE

The present invention relates to a process for the preparation of nucleoside diphosphate and triphosphate sugars, wherein the hydroxyl protective groups are removed enzymatically, as well as to the preparation of these sugars which comprises coupling a nucleotide with a sugar-1-phosphate activated with a carbonyl bisazole and then removing the hydroxyl protective groups enzymatically.

Aside from their importance as energy carriers and structural units, carbohydrates have an important part to play as information carriers in intercellular communication and in intercellular recognition processes. They are naturally obtained as poly-, oligo-, di- or monosaccharides or as glycoconjugates, typically glycoproteins, glycolipids and glycosteroids. Oligosaccharides and glycoconjugates may be built most efficiently by a combination of chemical and enzymatic methods. The key enzymes which are, inter alia, used here are the so-called glycosyltransferases of the Leloir pathway [Ichikawa, Y., Look, G. C., Wong, C. H., Anal. Biochem. 202:215–238 (1992)]. Said enxymes are distinguished by high regiospecificity and stereospecificity with respect to the glycoside bond to be linked.

The enzymes transfer a sugar unit of so-called activated nucleoside monophophate and diphosphate sugars (donors) to a very wide range of different acceptor substrates which are, however, specific for the respective enzyme. The donors are considered as limiting for this type of glycoside synthesis, in particular because it has so far not been possible to prepare these compounds simply, on a large scale and in high yield. One possible chemical synthesis consists in reacting an unprotected sugar phosphate with a nucleotide activated, for example by a morpholine group to the corresponding nucleoside diphosphate sugar [Gokhale, U. B., Hindsgaul, O., Palcic, M. M., Can. J. Chem. 68:1063–1071 (1990)]. This linkage of a pyrophosphate bond is highly susceptible to water and very difficult to carry out with unprotected educts owing to the hygroscopic hydroxyl groups. Furthermore, as the unprotected educts are only sparingly soluble in the conventional coupling solvents (dimethyl formamide, pyridine), long reaction times are required [Leon, B., Lindhorst, T. K., Rieks-Everdiking, A., Klaffke, W., Synthesis 689–691 (1994)]. In addition to forming undesirable by-products, many unprotected sugar phosphates are instable. In consequence, the yield is usually low and never above 50% [Nuñez, H. A. O'Connor, J. V., Rosevear, P. R., Barker, R., Can. J. Chem. 59:2086–2095 (1981); Gokhale, U. B., Hindsgaul, O., Palcic, M. M., Can. J. Chem. 68:1063–1071 (1990)]. Protected reagents have not been used so far because with the known processes it did not seem possible to completely remove the protective groups after the coupling step while retaining the desired target structure. Thus a guanosine diphosphate glucose which is O-benzoyl-protected at the carbon atoms 2 and 3 can only be debenzoylated with substantial decomposition. The complete removal of protective groups without decomposition has only been possible in the case of uncharged sugar atoms having no phosphate group [Waldmann, H., Sebastian, D., Chem. Rev. 94:911–937 (1994)]. An exception are certain O-acyl-protected uridine diphosphate hexoses, all of which carry a base-stable NHAc substituent at the carbon atom 2 of the hexose and are α-configurated at the carbon atom 1. They may be chemically deacylated with 1M sodium hydroxide [Yamazaki, T., Warren, C. D., Herscovics, A., Jeanloz, R. W., Carbohydr. Res. 79:C9–C12 (1980); Yamazaki, T., Warren, C. D., Herscovics, A., Jeanloz, R. W., Can. J. Chem. 59:2247–2252 (1981); Thomas, R. L., Abbas, S. A., Matta, K. L., Carbohydr. Res. 184:77–85 (1988)].

In addition to this possible chemical synthesis, specific naturally occuring donors can also be prepared using multienzyme systems. The great disadvantage of these enzyme systems is, however, that they are not easily available and can only be used on natural substrates [Heidlas, J. E., Lees, W. J., Pale, P., Whitesides, G. M., J. Org. Chem. 57:146–151 (1992)].

Surprisingly, it has now been found that nucleoside diphosphate and triphosphate sugars can be synthesised in high yield by using O-acyl protective groups in the sugar residue and, in the final reaction step, removing these protective groups under the action of specific enzymes. Accordingly it is also possible for the first time to carry out prior synthesis steps using reagents carrying protective groups, which is particularly useful for coupling the nucleotides to the sugar phosphate for the pyrophosphate bridge. The coupling proceeds in high yield and the coupling products can also be purified easily, are stable and can be stored. Starting from the sugar monomers it is thus possible to obtain a total yield which is substantially higher and which even permits economic preparation on an industrial scale.

In one of its aspects, the invention relates to a process for the preparation of nucleoside diphosphate or triphosphate sugars from protected nucleoside diphosphate or triphosphate sugars by complete removal of the hydroxyl protective groups of the formula —C(O)—R of the sugar residue, wherein R is linear or branched alkyl, preferably $C_1$–$C_8$alkyl, most preferably $C_1$–$C_4$alkyl, unsubstituted phenyl or $C_1$–$C_4$alkyl- or $C_1$–$C_4$alkoxy-substituted phenyl, which process comprises carrying out the removal enzymatically.

Illustrative examples of hydroxyl protective groups are protective groups of formula —C(O)—R, wherein R is methyl, ethyl, n- and i-propyl, n-, i-, s- and t-butyl as well as pentyl, hexyl, heptyl and octyl with all possible isomers, unsubstituted phenyl or phenyl which is substituted by 1 to 3 different or identical substituents selected from the group consisting of methyl, ethyl, n- and i-propyl, n-, i-, s- and t-butyl, methoxy, ethoxy, n- and i-propoxy, n-, i-, s- and t-butoxy. Typical examples of substituted phenyl derive from toluene, o-, m- and p-xylene, pseudocumol, mesitylene, trimetylbenzene, ethylenzene, dimethylpropylbenzene and cumol.

Within the scope of this invention, a sugar will be understood as meaning a sugar monomer or a sugar dimer, and in the case of the sugar dimer the sugar monomers are linked to one another α- or β-(anomeric center→n) glycosidically, n being a number from 1 to 9 and the term (anomeric center→n) indicating the positions of the glycosidic linkage of the two participating monomers.

Within the scope of this invention, monomeric sugars will be understood as meaning all compounds whose structure conforms to the formula $(CH_2O)_m$, where m is preferably a natural number from 3 to 9, as well as polyhydroxyaldehydes, polyhydroxyketones, polyhydroxyacids and polyhydroxyamines and derivatives thereof.

Sugar monomers are known from standard works of organic chemistry and biochemistry [e.g. Beyer/Walter, Lehrbuch der Organischen Chemie, S. Hirzel Verlag Stuttgart, 425–468 (1991); Lehninger, A. L., Biochemistry 298–321 (1993); Kennedy, J. F., White, C. A., in: Kennedy, J. F. (Hrsg.) Carbohydrate Chemistry, Clarendon Press, Oxford 3–41 (1988)].

Illustrative examples are sugar monomers selected from the group consisting of D- and L-aldopyranoses and D- and L-aldofuranoses, including ribose, arabinose, xylose, lyxose, allose, altrose, glucose, mannose, gulose, idose, galactose and talose, from the group consisting of D- and L-ketopyranoses and D- and L-ketofuranoses, typically including ribulose, xylulose, psicose, fructose, sorbose and tagatose, as well as from the group consisting of D- and L-diketopyranoses, typically pentodiulose and hexodiulose.

The term "sugar monomers" comprises also sugar monomers which represent substitutions of the cited examples. To those skilled in the art these sugar monomers typically include deoxy sugars of the D- and L-configuration, preferably 2-, 3-, 4- and 6-deoxyaldoses such as fucose, rhodeose, rhamnose and digitoxose, 1,2-dideoxyaldoses such as glucal, galactal and fucal, and 1-, 3-, 4- and 6-deoxyketoses, 2-, 3-, 4- and 6-deoxyamino sugars of the D-and L-configuration, typically glucosamine, mannosamine, galactosamine and fucosamine, deoxyacylamino sugars such as N-acylglucosamine, N-acylmannosamine, N-acylgalactosamine and N-acylfucosamine, preferably the $C_1$–$C_4$alkyl ester thereof, and 2-, 3-, 4- and 6-deoxyhalogeno sugars, where halogen is preferably F, Cl or Br, typically 2-fluorofucose, and 2-, 3-, 4- and 6-deoxysulfhydryl sugars and independent combinations of these substituents.

Sugar monomers will also be understood as meaning aldonic, aldaric and uronic acids such as gluconic acid or glucuronic acid, as well as amino acid-carrying sugar monomers which are N-amidically linked and those that carry the phosphatidyl or polyol substituents.

Substituted sugar monomers will also be understood as meaning those having a carbon chain longer than 6 carbon atoms, typically heptoses, octoses, nonoses, heptuloses, octuloses and nonuloses, and also the representatives substituted in accordance with the foregoing criteria, for example ketodeoxyoctanoic acid, ketodeoxynonanoic acid, N-acylneuraminic acids and N-acylmuraminic acids.

Preferred sugar monomers within the scope of this invention are arabinose, galactose, glucose, mannose, fucose, 2-fluorofucose, 2-aminofucose and rhodeose.

Within the scope of this invention, dimeric sugars will be understood as meaning those derived from two identical or different monomers cited above. The linkage is preferably α- or β-O-glycosidic, but S-, N- and C-glycosidic linkages are also possible. All carbon atoms of the one participant of a linkage are suitable. Illustrative examples are in particular (1→2)-, (1→3)-, (1→4)-, (1→5), (1→6), (2→3)- and (2→6) glycosidic linkages. Typical examples of dimeric sugars are those selected from the group consisting of trehalose, sophorose, kojibiose, laminaribiose, maltose, cellobiose, isomaltose, gentibiose, saccharose and lactose.

Within the scope of this invention, nucleosides will be understood as meaning natural and unnatural synthetic nucleosides. Synthetic nucleosides embrace the modifications of natural building blocks. Suitable modifications are modifications in the nucleic base residue (typically substitution, ommission of substituents) and in the furanose ring (typically substitutions at the 2'-hydroxyl group, replacement of the furanose-O-atom, replacement of the furanose ring with mono- or bicarbacyclic ring).

Particularly preferred nucleosides are guanosine, xanthosine, inosine, uridine, 2'-deoxy-2-aminoadenosine, 2'-deoxy-5-methylcytidine, 2'-dexoyadensoine, 2'-deoxycytidine, 2'-deoxyguanosine and thymidine. Guanosine, xanthosine, inosine and uridine are very particularly preferred. Modified building blocks are preferably derived from natural nucleosides of the purine and the pyrimidine series, particularly preferably from adenosine, cytidine, guanosine, 2-aminoadenosine, 5-methylcytidine, uridine and the deoxy derivatives cited above. The nucleosides can also be 2'-modified ribonucleosides.

The protected nucleoside diphosphate and triphosphate sugars are preferably compounds of formula I

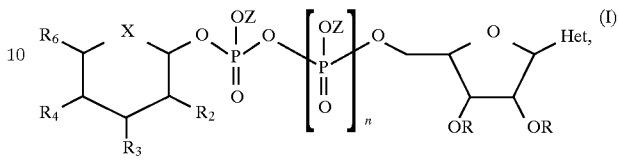

wherein n is 1 or 2,
X is an oxygen, sulfur or carbon atom,
Z is Na, K, Li or Mg,
$R_6$ is H or $CH_2R_7$,
$R_2$, $R_3$, $R_4$ and $R_7$ are each independently of one another H, halogen, preferably F, Cl or Br, SH, $NH_2$, NHR, or a radical —O—C(O)—R,
R is linear or branched $C_1$–$C_8$alkyl, unsubstituted phenyl or $C_1$–$C_4$alkyl- or $C_1$–$C_4$alkoxy-substituted phenyl, and
Het is a purine or pyrimidine base;
and the unprotected nucleoside diphosphate and triphosphate sugars are preferably compounds of formula II

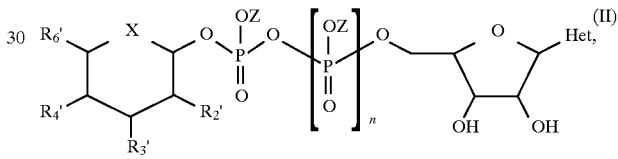

wherein
n, X, Z and Het have the meanings indicated in formula I;
$R_{6'}$ is H or $CH_2R_{7'}$,
$R_{2'}$, $R_{3'}$, $R_{4'}$ and $R_{7'}$ are each independently of one another H, halogen, preferably F, Cl or Br, SH, $NH_2$, NHR or OH,
R is linear or branched $C_1$–$C_8$alkyl, unsubstituted phenyl or $C_1$–$C_4$alkyl- or $C_1$–$C_4$alkoxy-substituted phenyl.

It has been found that those compounds of formula I are particularly useful, wherein X is an oxygen or carbon atom, preferably an oxygen atom, Z is Na, K, Li or Mg, preferably Na, $R_2$, $R_3$, $R_4$ and $R_6$ are each independently of one another a —OC(O)—R radical, R is linear or branched $C_1$–$C_4$akyl or phenyl, and Het is a purine or pyrimidine base. Particularly preferred compounds of formula I are those wherein R is methyl, ethyl, i- or n-propyl.

It is preferred to use nucleoside diphosphate and triphosphate sugars which are protected in the sugar residue and whose protective groups are identical.

Preferred nucleoside diphosphate and triphosphate sugars within the scope of this invention are guanosine diphosphate fucose, xanthosine diphosphate fucose, inosine diphosphate fucose, guanosine diphosphate-2-fluorofucose, guanosine diphosphate-β-L-2-aminofucose, guanosine triphosphate fucose, guanosine, diphosphate-D-arabinose, guanosine diphosphate-β-L-galactose, uridine diphosphate galactose, guanosine diphosphate-β-L-glucose, guanosine diphosphate-α-D-mannose and guanosine diphosphate-β-D-rhodeose.

The novel process can be carried out with soluble or immobilised enzymes. The choice of enzyme depends on the type of protective groups and on the stereochemistry at the sugar. It has been found useful to work with a functionally homogenous enzyme or an enzyme mixture.

If the protective group is a —C(O)—CH$_3$ radical, then the protective group is removed with an acetylesterase. If the protective group is a —C(O)—CH$_2$CH$_3$ radical, then the protective group is removed with an acetylesterase, a lipase or a mixture of these two enzymes. To remove the —C(O)—C$_3$–C$_8$alkyl and unsubstituted or substituted —C(O)-phenyl the use of lipases is preferred. The enzymes may originate from natural sources, such as animals, microorganisms or plants, but may also result from genetic engineering. Commercially available enzymes are particularly convenient, typically vegetable enzymes, such as the acetylesterase from orange peel (EC 3.1.1.6).

The reaction may proceed in the presence of buffers but also, surprisingly, in their absence. If buffers are present, then these are conveniently electrolytic buffers, typically NaCl, MgHPO$_4$, 2-morpholinoethanesulfonic acid monohydrate-NaOH, N-(2-acetamino)-2-aminoethanesulfonic acid-NaOH—NaCl, 3-morpholinopropanesulfonic acid-NaOH—NaCl, N-tris(hydroxymethyl)methyl-2-aminoethanesulfonic acid-NaOH—NaCl, 4-(2-hydroxyethyl)piperazine-1-ethanesulfonic acid-NaOH—NaCl and imidazole-HCl—NaCl. The reaction is preferably carried out in the temperature range from room temperature to 40° C., preferably at 37° C. The pH is conveniently in the range from pH 6.5 and pH 7.5, preferably at pH 7, and is usefully kept constant automatically, e.g. by the aid of pH probes and automatic metering units. Furthermore, the choice of buffer, temperature and pH is determined by the respective enzyme used and the substrate to be reacted and in particular cases it may well lie beyond the indicated realms.

The invention also relates to a process for the preparation of nucleoside diphosphate or triphosphate sugars from protected nucleoside diphosphate or triphosphate sugars by complete removal of the hydroxyl protective groups of the formula —C(O)—R of the sugar residue, wherein R is linear or branched alkyl, preferably C$_1$–C$_8$alkyl, most preferably C$_1$–C$_4$alkyl, unsubstituted phenyl or C$_1$–C$_4$alkyl- or C$_1$–C$_4$alkoxy-substituted phenyl, which process comprises carrying out the removal enzymatically in the absence of buffers.

The product can easily be purified after the removal of the protective groups. If the protective groups are removed in the presence of buffers, then chromatographic methods are particularly suitable. The product can be desalted via gel permeation chromatography, typically over a Sephadex® column, e.g. Biogel P-2, and then reacted direct with a glycosyl acceptor in the presence of a glycosyltransferase. If the removal of the enzymatic protective group is carried out in the absence of buffers, then the unprotected product may be purified by precipitation with suitable precipitating agents, typically ethanol or mixtures of ethanol/isopropanol or ethanol/acetone.

The yield obtained in accordance with the novel process is substantially enhanced. Hitherto it has, for example, not been possible to obtain a preparatively viable multienzyme system for the preparation of guanosine diphosphate-β-L-fucose [Yamamoto, K., Maruyama, T., Kumagai, H., Tochikura, T., Seno, T., Yamaguchi, H., Agric. Biol. Chem. 48:823–824 (1984); Stiller, R., Thiem, J., Liebigs Ann. Chem. 467–471 (1992)], so that said nucleoside diphosphate sugar still had to be synthetised chemically. Starting from L-fucose, said sugar could be obtained in about 10% total yield [Gokhale, U. B., Hindsgaul, O., Palcic, M. M., Can. J. Chem. 68:1063–1071 (1990)]. Here the linkage of the diphosphate bond was carried out using unprotected and very instable fucose-1-phosphate. To process the final product, a total of 9 chromatographic purification steps were required. In contrast, the total yield of the novel process is usually above 50%.

In another of its aspects, the invention relates to a process for the preparation of nucleoside diphosphate or triphosphate sugars, wherein a protected sugar-1-phosphate is reacted with a nucleoside monophosphate or diphosphate, which process comprises activating either the sugar-1-phosphate or the corresponding nucleoside prior to coupling it with a carbonyl bisazole and, after coupling has been carried out, removing the protective groups enzymatically.

The preparation of monoimidazolyl phosphonates using carbonyl diimidazole and the use thereof for the formation of symmetric and unsymmetric pyrophosphates is known [Schaller, H., Staab, H. A., Cramer, F., Chem. Ber. 94:1621–1633 (1961)].

Typical examples of carbonyl bisazoles are carbonyl diimidazole, carbonyl ditriazole, thiocarbonyl diimidazole and carbonyl dioxydibenzotriazole.

Protected monophosphoric acid sugar esters are, for example, reacted in the presence of a polar solvent with an excess of carbonyl bisazole. Excess carbonyl diazole is then destroyed, conveniently using a precise amount of absolute methanol. After this activation, the activated sugar phosphates are reacted in situ, or after isolating them with trialkylammonium salts of the nucleotide building blocks, to the protected nucleoside diphosphate or triphosphate sugars. The imidazole salt initailly obtained is then filtered over a ion exchanger to exchange it for any ion Z. Subsequent purification can their be carried out over reversed phase silica or by precipitation using suitable precipitating agents, typically ethanol or mixtures of ethanol/isopropanol or ethanol/acetone. The reaction is usefully carried out in the absence of water in an anhydrous polar non-hydroxylic solvent in the temperature range from room temperature to 80° C., preferably in the range from 40° C. to 50° C., most preferably at 40° C. It has been found useful to carry out the reaction in an ultrasonic bath.

Typical examples of polar non-hydroxylic solvents are dimethyl formamide, dimethyl sulfoxide, acetone, dioxane, pyridine and acetonitrile as well as mixtures thereof.

The unprotected compounds obtained according to the novel process serve as donors for different glycosyltransferases of the Leloir pathway (see above). In the course of this pathway the sugar residue of the nucleoside diphosphate or triphosphate sugar is transferred to an acceptor. This acceptor may be a sugar, an amino acid of a protein, or the OH group of a lipid, steroid or macrocycle. The products obtained are pharmacologically very interesting because they can be used to selectively influence, for example, adhesion processes (e.g. blocking the adhesion of leucozytes at activated endothelial cells), to detect specific pathological cell types or proteins (diagnostics) or to modulate immune reactions [Seyfried, T. N., Developmental Biology 123:286–291 (1987); Hakomori, S., Cancer Res. 45:2405 (1985); Bock, K., Clausen, H. (Hrsg.), Complex Carbohydrates in Drug Research, Alfred Benzon Symposium 36, Munksgaard, Copenhagen (1994) 118–130, 153–164, 246–256, 280–290, 297–310, 337–349, 366–367, 368–379, 382–393, 397–409, 414–427].

The following Examples illustrate the invention in more detail.

EXAMPLE 1

Preparation of guanosine diphosphate fucose (GDP-fucose) (method A)

(a) 605 mg (1.63 mmol) of tri-O-acetyl-β-L-fucose-1-phosphate, obtainable in accordance with the process of Ichikawa, Y., Sim, M. M., Wong, C.-H., J. Org. Chem. 57:2943–2946 (1992), are dissolved in 3 ml of absolute dimethyl formamide. To this solution are added 390 mg (2.49 mmol) of carbonyl diimidazole and the clear solution is stirred for 90 minutes at room temperature. Excess carbonyl diimidazole is then destroyed with 0.86 mmol of absolute methanol. After stirring for 20 minutes at room temperature, some of the solvent is removed under high-vacuum. A solution of 781 mg (1.80 mmol) of the tributylammonium salt of guanosine-1-phosphate in 4 ml dimethyl formamide is then rapidly added dropwise. The resulting suspension is sonicated over 24 hours in an ultrasonic bath at 40° C. The resulting solution is concentrated by evaporation to dryness at 40° C. and the residue is lyophilised from dioxane. The lyophilisate is filtered over a DOWEX column (Na$^\oplus$ form) and the fractions containing the product are combined, concentrated and lyophilised once more from dioxane. The powder obtained is purified on RP-18 gel, giving 950 mg (68%) of GDP-2,3,4-tri-O-acetyl-β-L-fucose in the form of a white powder.

$^1$H-NMR (D$_2$O, 250.134 MHz, in ppm about D$_2$O, 4.8 ppm): 1.20 d, 8.2 Hz, 3H; 2.03 s, 3H; 2.17 s, 3H; 2.24 s, 3H; 4.02 dq, 1.8 Hz, 8.2 Hz, 1H; 4.24 m, 2H; 4.41 m, 4.54 m, 1H; 5.11 m, 2H; 5.36 m, 2H; 5.95 d, 6.9 Hz, 1H; 8.14 s, 1H.

$^{13}$C-NMR (D$_2$O, 62.896 Hz): 18.52 ppm, 23.50 ppm (2×C), 23.95 ppm, 68.80 ppm, 73.40 ppm (d, 8.73 Hz), 73.64 ppm, 73.68 ppm, 74.25 ppm, 77.48 ppm, 87.02 ppm (d, 9.2 Hz), 99.00 ppm (d, 4.5 Hz), 119.57 ppm, 141.06 ppm, 155.11 ppm, 157.41 ppm, 162.28 ppm, 176.24 ppm, 176.76 ppm, 177.18 ppm $^{31}$P-NMR (D$_2$O, 101.256 Hz): −11.31 ppm, d, 18.17 Hz; −13.40 ppm, d, 18.17 Hz.

(b) 649 mg (85 μmol) of GDP-2,3,4-tri-O-acetyl-β-L-fucose are dissolved in 2.4 ml of a 0.075N NaCl solution at pH 6.78 and to this solution are added 1.6 ml of a acetylesterase solution (75 U, orange-peel, 3.1.1.6, Sigma). The pH of the reaction mixture is kept constant at 6.78 with a 1.N NaOH solution. The reaction is carried out at room temperature and with stirring. The reaction is stopped at a consumption of 24.82 ml of 0.1N NaOH solution (theoretically 25.5 ml). The reaction mixture is desalted over a biogel P-2 column (3 cm×74 cm) and the eluants containing GDP fucose are combined and lyophilised, giving 540 mg of powdered GDP-fucose.

$^1$H-NMR (D$_2$O, 250.134 Hz): 1.21 d (8.2 Hz), 3H; 3.52 dd (8.3 Hz, 10.3 Hz), 1H; 3.66 m, 2H; 3.74 dq (1.8 Hz, 8.2 Hz), 1H; 4.24 m, 2H; 4.41 m, 1H; 4.54 dd (3.4 Hz, 5.5 Hz), 1H; 5.95 d (6.9 Hz), 1H; 8.14 s, 1H.

$^{31}$P-NMR (101.256 Hz): −12.70 ppm, d, 20.03 Hz; −10.86 ppm, d, 20.03 Hz.

EXAMPLE 2

Preparation of guanosine diphosphate fucose (GDP-fucose) (method B)

(a) 3.0 g (5.5 mmol) of tributylammonium salt of guanosine monophosphate are dissolved in 36 ml of anhydrous dimethyl formamide under argon at room temperature. To this solution are added, with stirring, 1.9 g (11.7 mmol) of carbonyl diimidazole and stirring is continued for a further 40 minutes at room temperature. This mixture is then injected with 195.5 μl of dry methanol, stirred for 20 minutes and then a high vacuum is applied for 15 minutes. After the dropwise addition of 2.55 g (6.9 mmol) of tri-O-acetyl-β-L-fucose-1-phosphoric acid, dissolved in 48 ml of dry dimethyl formamide, the reaction mixture is stirred for 40 h.

When the reaction is complete, the solvent is removed at c. 40° C. under high vacuum, the residue is taken up in water and fractionated over a DOWEX-S column (Na$^+$-Form, 7 cm×35 cm). The fractions containing sugar are combined and lyophilised. The resulting powder (5.2 g) is dissolved in 80 ml of water and then 2100 U (140 μl) of calf intestine alkaline phosphatase (Boehringer) are added and stirred overnight at pH=7.7. The mixture is concentrated at c. 40° C. to about 50 ml and diluted with 250 ml of ethanol. The residue is centifuged off, washed with 100 ml of ethanol and lyophilised from dioxane/water, giving 3.6 g (87%) of tri-O-acetyl-GDP-fucose. The spectrographic data of this material are identical with those of the product of Example 1.

(b) 500 mg (660 μmol) of tri-O-acetyl-GDP-fucose are dissolved in 3 ml of water and incubated at 37° C. with 250 U of pretreated acetylesterase (75 U, orange-peel, 3.1.1.6, Sigma; pretreatment by a c. 3.5 h dialysis against 6×1 l of bidistilled water) dissolved in 3 ml of water. The pH of the reaction mixture is kept at 6.8 with 0.1 m of sodium hydroxide solution and pH dosimate. After consumption of the theoretical amount of sodium hydroxide solution, the solution is diluted with 150 ml of ethanol, the precipitate is centrifuged off, taken up in 25 ml of water and filtered over an AMICON filter (YM-10). The filtrate is lyophilised, giving 382 mg (92%) of GDP-fucose. This product is identical with the one obtained according to Example 1. The UV spectrum of a sample shows a 97% GDP-fucose content.

EXAMPLE 3

Preparation of xanthosine diphosphate fucose (XDP-fucose) (method B)

(a) In general accordance with the general procedure of Example 2, 535 mg (59%) of XDP-2,3,4-tri-O-acetyl-β-L-fucose are obtained in the form of a white powder from 667 mg (1.2 mmol) of tributylammonium salt of xanthosine monophosphate, 335 mg (2.1 mmol) of carbonyl diimidazole and 450 mg (1.8 mmol) of tri-O-acetyl-β-L-fucose-1-phosphoric acid.

$^1$H-NMR (D$_2$O, 250.134 MHz, ppm relative to D$_2$O: 4.8ppm): 1.20d, 8.2 Hz, 3H; 2.04 s, 3H; 2.17 s, 3H; 2.23 s, 3H; 4.01 dq, ~1 Hz, 8.2 Hz, 1H; 4.25 m, 2H; 4.37 m, 1H; 4.68 m, 1H; 5.21 m, 4H; 5.95 d, 6.9 Hz, 1H; 8.09 s, 1H.

$^{31}$P-NMR(D$_2$O, 101.256 MHz): −11.30 ppm, d, 18.33 Hz; −13.44 ppm, d, 18.33 Hz.

(b) The entire sample is deacetylised enzymatically in accordance with Example 2, giving 430 mg (total yield: 56%) of XDP-fucose in the form of a white powder. The UV spectrum of a sample shows a 100% XDP-fucose content.

$^1$H-NMR (D$_2$O, 250.134 MHz, ppm relative to D$_2$O: 4.8 ppm): 1.23 d, 8.2 Hz, 3H; 3.69 m, 4H; 4.21 m, 2H; 4.37 m, 1H; 4.52 m, 1H; 4.68 m, 1H; 4.90 dd, 2.7 Hz, 8.3 Hz, 1H; 5.93 d, 6.9 Hz, 1H; 8.06 s, 1H.

$^{31}$P-NMR(D$_2$O, 101.256 MHz): −11.12 ppm, d, 19.54 Hz; −12.98 ppm, d, 19.54$_2$ Hz.

EXAMPLE 4

Preparation of inosine diphosphate fucose (IDP-fucose) (method B)

(a) In general accordance with the procedure of Example 2, 632 mg (70%) of IDP-2,3,4-tri-O-acetyl-β-L-fucose are obtained in the form of a white powder from 648 mg (1.2 mmol) of tributylammonium salt of inosine monophosphate, 335 mg (2.1 mmol) of carbonyl diimidazole and 450 mg (1.8 mmol) of tri-O-acetyl-β-L-fucose-1-phosphoric acid.

$^1$H-NMR (D$_2$O, 250.134 MHz, ppm relative to D$_2$O; 4.8ppm): 1.21 d, 7.6 Hz, 3H; 2.02 s, 3H; 2.16 s, 3H; 2.24 s, 3H; 4.15 dq, 1.5 Hz, 7.6 Hz, 1H; 4.27 m, 2H; 4.42 m, 1H; 4.57 m, 1H; 4.69 m, 1H; 5.15 m, 2H; 5.30 m, 2H; 6.16 d, 6.9 Hz, 1H; 8.22 s, 1H; 8.49 s, 1H.

$^{31}$P-NMR(D$_2$O, 101.256 MHz): −11.42 ppm, d, 19.20 Hz; −13.50 ppm, d, 19.20 Hz.

(b) The entire sample is deacetylated enzymatically in general accordance with the procedure of Example 2, giving 440 mg (total yield: 59%) of IDP-fucose in the form of a white powder. The UV spectrum of a sample shows a 97% IDP-fucose content.

$^1$H-NMR (D$_2$O, 250.134 MHz, ppm relative to D$_2$O: 4.8ppm): 1.20 d, 7.6 Hz, 3H; 3.56 dq, 1.5 Hz, 7.6 Hz, 1H; 3.72 m, 3H; 4.22 m, 2H; 4.40 m, 1H; 4.53 m, 1H; 4.91 dd, 2.7 Hz, 7.6 Hz, 1H; 6.19 d, 6.9 Hz, 1H; 8.17 s, 1H; 8.42 s, 1H.

$^{31}$P-NMR (D$_2$O, 101.256 MHz): −11.13 ppm, d, 18.60 Hz; −12.93 ppm, d, 18.60 Hz.

EXAMPLE 5

Preparation of guanosine diphosphate-D-arabinose (GDP-arabinose) (method B)

(a) In general accordance with the procedure of Example 2, 553 mg (85%) of GDP-2,3,4-tri-O-acetyl-β-D-arabinose are obtained in the form of a white powder from 451 mg (0.9 mmol) of tributylammonium salt of guanosine monophosphate, 286 mg (1.7 mmol) of carbonyl diimidazole and 370 mg (1.0 mmol) of tri-O-acetyl-α-D-arabinose-1-phosphoric acid.

$^1$H-NMR (D$_2$O, 250.134 MHz, ppm relative to D$_2$O: 4.8 ppm): 2.01 s, 3H; 2.12 s, 6H; 3.84 dd, 1.4 Hz, 13.1 Hz, 1H; 4.02 dd, 3.4 Hz, 13.1 Hz, 1H; 4.21 m, 2H; 4.32 m, 1H; 4.48 m, 1H; 4.70 m, 1H; 5.21 m, 4H; 5.87 d, 6.9 Hz, 1H; 8.03 s, 1H.

$^{31}$P-NMR (D$_2$O, 101.256 MHz): −11.41 ppm, d, 19.30 Hz; −13.59 ppm, d, 19.30 Hz.

(b) 518 mg of this sample are deacetylated enzymatically in general accordance with the procedure of Example 2, giving 418 mg (total yield: 77%) of GDP-arabinose in the form of a white powder. A UV spectrum confirms a 99% GDP-arabinose content.

$^1$H-NMR (D$_2$O, 250.134 MHz, ppm relative to D$_2$O: 4.8 ppm): 3.69 m, 3H; 3.94 m, 2H; 4.22 m, 2H; 4.35 m, 1H; 4.52 m, 1H; 4.75 m, 2H; 4.82 m, 1H; 5.89 d, 6.9 Hz, 1H; 8.09 s, 1H.

$^{31}$P-NMR (D$_2$O, 101.256 MHz): −11.10 ppm, d, 16.6 Hz; −12.85 ppm, d, 16.6 Hz.

EXAMPLE 6

Preparation of guanosine diphosphate-β-L-galactose (GDP-galactose) (method B)

(a) In general accordance with the procedure of Example 2, 575 mg (71%) of GDP-2,3,4,6-tetra-O-acetyl-β-L-galactose are obtained in the form of a white powder from 507 mg (0.9 mmol) of tributylammonium salt of guanosine monophosphate, 322 mg (1.9 mmol) of carbonyl diimidazole and 500 mg (1.2 mmol) of tetra-O-acetyl-β-L-galactose-1-phosphoric acid.

$^1$H-NMR (D$_2$O, 250.134 MHz, ppm relative to D$_2$O: 4.8 ppm): 1.98 s, 3H; 2.02 s, 3H; 2.13 s, 3H; 2.16 s, 3H; 4.16 m, 5H; 4.22 m, 1H; 4.49 m, 1H; 5.11 m, 1H, 5.30 m, 1H; 5.40 m, 1H; 5.89 d, 6.9 Hz, 1H; 8.09 s, 1H.

$^{31}$P-NMR (D$_2$O, 101.256 MHz): −11.34 ppm, d, 18.6 Hz; −13.69 ppm, d, 18.6 Hz.

(b) The entire sample is deacetylated enzymatically in accordance with Example 2, giving 294 mg (total yield: 46%) of GDP-galactose in the form of a white powder. A UV spectrum of this sample confirms a 100% GDP-galactose content.

$^1$H-NMR (D$_2$O, 250.134 MHz, ppm relative to D$_2$O: 4.8 ppm): 3.63 m, 5H; 3.92 d, 2.8 Hz, 1H; 4.27 m, 2H; 4.49 m, 1H; 4.58 m, 1H; 4.95 t, 7.5 Hz 1H; 5.95 d, 6.9 Hz, 1H; 8.12 s, 1H.

$^{31}$P-NMR (D$_2$O, 101.256 MHz): −11.19 ppm, d, 20.2 Hz; −12.89 ppm, d, 20.2 Hz.

$^{31}$C-NMR (D$_2$O, 62.896 MHz, in ppm): 63.30; 67.45 d; 70.70; 72.48; 73.32 d; 74.36; 75.92; 77.96; 85.80 d; 88.88; 100.58 d; 118.19; 139.53; 153.77; 155.94; 160.91.

EXAMPLE 7

Preparation of guanosine diphosphate-β-L-glucose (GDP-glucose) (method B)

(a) In general accordance with the procedure of Example 2, 640 mg (80%) of GDP-2,3,4,6-tetra-O-acetyl-β-L-glucose are obtained in the form of a white powder from 507 mg (0.9 mmol) of tributylammonium salt of guanosine monophosphate, 322 mg (1.9 mmol) of carbonyl diimidazole and 500 mg (1.2 mmol) of tetra-O-acetyl-β-L-glucose-1-phosphoric acid.

$^1$H-NMR (D$_2$O, 250.134 MHz, ppm relative to D$_2$O: 4.8 ppm): 2.04 s, 3H; 2.05 s, 3H; 2.08 s, 3H; 2.13 s, 3H; 3.94 m, 1H; 4.10 dd, 1.4 Hz, 12.4 Hz, 1H; 4.23 m, 3H; 4.32 m, 1H; 4.49 dd, 1.3 Hz, 5.5 Hz, 1H; 5.00 t, 7.6 Hz, 1H; 5.08 t, 8.9 Hz, 1H; 5.25 t, 8.9 Hz, 1H; 5.31 t, 8.2 Hz, 1H; 5.92 d, 6.9 Hz, 1H; 8.11 s, 1H.

$^{31}$P-NMR (D$_2$O, 101.256 MHz): −11.39 ppm, d, 19.4 Hz; −13.86 ppm, d, 19.4 Hz.

(b) The entire sample is deacetylated enzymatically in accordance with the procedure of Example 2, giving 290 mg (total yield: 46%) of GDP-glucose in the form of a white powder. A UV spectrum of this sample confirms a 100% GDP-glucose content.

$^1$H-NMR (D$_2$O, 250.134 MHz, ppm relative to D$_2$O: 4.8 ppm): 3.34 m, 2H; 3.46 m, 2H; 3.67 dd, 6.2 Hz, 12.4 Hz, 1H; 3.85 dd, 1.4 Hz, 12.4 Hz, 1H; 4.21 m, 2H; 4.43 m, 1H; 4.51 m, 1H; 4.75 t, 5.5 Hz, 1H; 4.94 t, 6.9 Hz, 1H; 5.87 d, 6.9 Hz, 1H; 8.06 s, 1H.

$^{31}$P-NMR (D$_2$O, 101.256 MHz): −11.20 ppm, d, 20.1 Hz; −12.94 ppm, d, 20.1 Hz.

$^{13}$C-NMR (D$_2$O, 62.896 MHz, in ppm): 63.28; 67.84 d; 71.93; 72.93; 76.13 d; 76.27; 77.67; 79.01; 86.26 d; 89.32; 100.42 d; 118.68; 140.03; 154.23; 156.39; 161.40.

EXAMPLE 8

Preparation of guanosine diphosphate-2-fluorofucose (GDP-2F-fucose) (method B)

(a) In general accordance with the procedure of Example 2, 274 mg (100%) of GDP-3,4-di-O-acetyl-2-fluoro-β-L-fucose are obtained in the form of a white powder from 197 mg (0.4 mmol) of tributylammonium salt of guanosine monophosphate, 125 mg (0.7 mmol) of carbonyl diimidazole and 150 mg (0.4 mmol) of di-O-acetyl-2-fluoro-β-L-fucose-1-phosphoric acid.

¹H-NMR (D₂O, 250.134 MHz, ppm relative to D₂O: 4.8 ppm): 1.19 d, 7.6 Hz, 3H; 2.06 s 3H; 2.21 s, 3H; 4.41 q, 7.6 Hz, 1H; 4.23 m, 2H; 4.35 m, 1H; 4.53 m; 2H; 4.76 t, 5.5 Hz, 1H; 5.37 m, 3H; 5.93 d, 6.9 Hz, 1H; 8.11 s, 1H;

³¹P-NMR (D₂O, 101.256 MHz); −11.05 ppm, d, 19.2 Hz; −13.19 ppm, d, 19.2 Hz.

(b) The entire sample is deacetylated enzymatically in accordance with the procedure of Example 2, giving 191 mg (total yield: 80%) of GDP-2F-gucose in the form of a white powder. A UV spectrum of this sample confirms a 100% product content.

¹H-NMR (D₂O, 250.134 MHz, ppm relative to D₂O: 4.8 ppm): 1.21 d, 7.6 Hz, 3H; 3.79 m, 2H; 4.00 m, 1H; 4.21 m, 2H; 4.26 m, 1H; 4.35 m, 1H; 4.50 m, 2H; 5.16 m, 1H; 5.91 d, 6.9 Hz, 1H; 8.09 s, 1H.

³¹P-NMR (D₂O, 101.256 MHz): −11.29 ppm, d, 19.5 Hz; −13.23 ppm, d, 19.5 Hz.

¹³C-NMR (D₂O, 100.62 MHz, in ppm): 65.61 d; 70.78; 71.54 d; 71.99 d; 72.05; 74.00; 84.10 d; 87.13; 90.94 dd; 95.78 dd; 116.48; 137.85; 152.04; 154.29; 159.31.

¹⁹F-NMR (D₆-DMSO, 235.36 MHz): −205.79 ppm,

EXAMPLE 9

Preparation of uridine diphosphate galactose (UDP-galactose) (method B)

(a) In general accordance with the procedure of Example 2, 350 mg (55%) of UDP-2,3,4,6-tetra-O-acetyl-α-D-galactose are obtained in the form of a white powder from 426 mg (0.8 mmol) of tributylammonium salt of uridine monophosphate, 225 mg (1.4 mmol) of carbonyl diimidazole and 350 mg (0.8 mmol) of tetra-O-acetyl-α-D-galactose-1-phosphoric acid. Here the product remains soluble in the ethanol/water phase so that the impurities are centrifuged off as precipitate.

(b) The entire sample is deacetylated enzymatically in general accordance with the procedure of Example 2, giving 133 mg (total yield: 27%) of UDP-galactose in the form of a white powder.

The ¹H-NMR data correspond to the literature references for this compound [Heidlas, J. E., Lees, W. J., Pale, P., Whitesides, G. M., J. Org. Chem. 57:146–151 (1992)].

EXAMPLE 10

Preparation of guanosine triphosphate fucose (GTP-fucose) (method B)

(a) In general accordance with the procedure of Example 2, 240 mg (60%) of GTP-2,3,4-tri-O-acetyl-β-L-fucose are obtained in the form of a white powder from 300 mg (0.5 mmol) of tributylammonium salt of guanosine diphosphate, 165 mg (1.0 mmol) of carbonyl diimidazole and 221 mg (0.6 mmol) of tri-O-acetyl-β-L-fucose-1-phosphoric acid.

¹H-NMR (D₂O, 250.134 MHz, ppm relative to D₂O: 4.8 ppm): 1.18 d, 7.6 Hz, 3H; 1.98 s, 3H; 2.12 s, 3H; 2.19 s, 3H; 4.10 q, 7.6 Hz, 1H; 4.25 m, 2H; 4.35 m, 1H; 4.51 m, 1H; 4.75 m, 1H; 5.20 m, 4H; 5.87 d, 6.9 Hz, 1H; 8.06 s, 1H.

³¹P-NMR (D₂O, 101.256 MHz): −11.16 ppm, d, 17.7 Hz; −13.28 ppm, d, 16.0 Hz; −22.72 ppm, broad t, 16.5 Hz.

(b) The entire sample is deacetylated enzymatically in accordance with the procedure of Example 2, giving 133 mg (total yield: 35%) of GTP-fucose in the form of a white powder. A UV spectrum of this sample confirms a 98% product content.

¹H-NMR (D₂O, 250.134 MHz, ppm relative to D₂O: 4.8 ppm): 1.26 d, 7.6 Hz, 3H; 3.66 m, 3H; 3.71 q, 7.6 Hz, 1H; 4.27 m, 2H; 4.49 m, 1H; 4.58 m, 1H; 4.97 m, 1H; 5.92 d, 6.9 Hz, 1H; 8.01 s, 1H.

³¹P-NMR (D₂O, 101.256 MHz): −11.53 ppm, d, 17.6 Hz; −13.09 ppm, d, 16.4 Hz; −22.77 ppm, t, 16.8 Hz.

¹³C-NMR (D₂O, 100.61 MHz, in ppm): 15.72; 65.63 d; 70.65; 71.25 d; 7143; 71.76; 72.73; 74.06; 84.00 d; 86.96; 98.40 d; 119.33; 136.88; 151.50; 153.60; 159.00.

EXAMPLE 11

Preparation of guanosine diphosphate-α-D-mannose (GDP-mannose) (method B)

(a) In general accordance with the procedure of Example 2, 631 mg (79%) of GDP-2,3,4,6-tetra-O-acetyl-α-D-mannose are obtained in the form of a white powder from 508 mg (1.0 mmol) of tributylammonium salt of guanosine monophosphate, 323 mg (1.9 mmol) of carbonyl diimidazole and 500 mg (1.2 mmol) of tetra-O-acetyl-α-D-mannose-1-phosphoric acid.

¹H-NMR (D₂O, 250.134 MHz, ppm relative to D₂O: 4.8 ppm): 1.99 s, 3H; 2.07 s, 3H; 2.12 s, 3H; 2.19 s, 3H; 4.03 d, 11.0 Hz, 1H; 4.25 m, 2H; 4.37 m, 3H; 4.50 m, 1H; 4.77 t, 6.9 Hz, 1H; 5.25 t, 9.6 Hz, 1H; 5.38 dd, 2.8 Hz. 10.3 Hz, 1H; 5.61 d, 10.3 Hz, 1H; 5.94 d, 6.9 Hz, 1H, 8.13 s, 1H.

³¹P-NMR (D₂O, 101.256 MHz): −11.42 ppm, d, 20.2 Hz; −14.46 ppm, d, 20.2 Hz.

(b) The entire sample is deacetylated enzymatically in accordance with the procedure of Example 2, giving 479 mg (total yield: 75%) of GDP-mannose in the form of a white powder.

¹H-NMR (D₂O, 250.134 MHz, ppm relative to D₂O: 4.8 ppm): 3.83 m, 5H; 4.09 m, 1H; 4.25 m, 2H; 4.49 m, 1H; 4.52 t, 4.2 Hz, 1H; 5.52 dd, 2.1 Hz, 7.6 Hz, 1H; 5.94 d, 6.9 Hz, 1H; 8.10 s, 1H.

³¹P-NMR (D₂O, 101.256 MHz): −11.16 ppm, d, 20.2 Hz; −13.74 ppm, d, 20.2 Hz.

¹³C-NMR (D₂O, 62.896 MHz, in ppm): 63.35; 67.84 d; 72.43; 72.91 d; 72.94; 76.29; 76.41; 86.22 d; 89.47; 99.03 d; 118.73; 154.19; 156.48; 161.48.

EXAMPLE 12

Preparation of guanosine diphosphate-β-L-2-amino-fucose (GDP-2-NH₂-fucose) (method B)

(a) In general accordance with the procedure of Example 2, 300 mg (56%) of GDP-2-amino-3,4-di-O-acetyl-β-L-fucose are obtained in the form of a white powder from 398 mg (0.8 mmol) of tributylammonium salt of guanosine monophosphate, 252 mg (1.6 mmol) of carbonyl diimidazole and 300 mg (0.9 mmol) of 2-amino-3,4-di-O-acetyl-βL-fucose-1-phosphoric acid.

¹H-NMR (D₂O, 250.134 MHz, ppm relative to D₂O: 4.8 ppm): 1.19 d, 7.6 Hz, 3H; 2.09 s, 3H; 2.22 s, 3H; 3.01 dd, 8.3 Hz, 10.3 Hz, 1H; 4.00 q, 7.6 Hz, 1H; 4.28 m, 2H; 4.49 m, 1H; 4.56 m, 1H; 4.91 m, 1H; 5.08 t, 8.3 Hz, 1H; 5.21 d, 3.4 Hz, 1H; 5.97 d, 6.9 Hz, 1H; 8.14 s, 1H.

³¹P-NMR (D₂O, 101.256 MHz): −11.30 ppm, d, 20.3 Hz; −13.14 ppm, d, 20.3 Hz.

(b) 85 mg of this sample are deacetylated enzymatically in general accordance with the procedure of Example 2, giving 70 mg (94%) of GDP-2-NH₂-fucose in the form of a white powder. A UV spectrum of this sample confirms a 95% product content.

$^1$H-NMR (D$_2$O, 250.134 MHz, ppm relative to D$_2$O: 4.8 ppm): 1.22 d, 7.6 Hz, 3H; 3.17 dd, 8.3 Hz, 10.3 Hz, 1H; 3.68 m, 3H; 4.20 m, 2H; 4.50 m, 1H; 4.71 m, 1H; 5.17 t, 6.9 Hz, 1H; 5.88 d, 6.9 Hz, 1H; 8.06 s, 1H.

$^{31}$P-NMR (D$_2$O, 101.256 MHz): −11.19 ppm, d, 20.3 Hz; −13.57 ppm, d, 20.3 Hz.

EXAMPLE 13

Preparation of guanosine diphosphate-β-D-rhodeose (GDP-rhodeose) (method B)

(a) In general accordance with the procedure of Example 2, 750 mg (93%) of GDP-2,3,4-tri-O-acetyl-β-D-rhodeose are obtained in the form of a white powder from 586 mg (1.0 mmol) of tributylammonium salt of guanosine monophosphate, 372 mg (1.7 mol) of carbonyl diimidazole and 500 mg, (1.3 mmol) of tri-O-acetyl-β-D-rhodeose-1-phosphoric acid.

$^1$H-NMR (D$_2$O, 250.134 MHz, ppm relative to D$_2$O: 4.8 ppm): 1.19 d, 7.6 Hz, 3H; 2.03 s, 3H; 2.14 s, 3H; 2.23 s, 3H; 4.07 dq. 1 Hz; 7.6 Hz, 1H; 4.22m, 2H; 4.38 m, 1H; 4.54 m, 1H; 5.24 m, 4H; 5.95 d, 6.9 Hz, 1H; 8.02 s, 1H.

$^3$P-NMR (D$_2$O, 101.256 MHz): −11.30 ppm, d, 18.5 Hz; −13.40 ppm, d, 18.5 Hz.

(b) 740 mg of this sample are deacetylated enzymatically in general accordance with the procedure of Example 2, giving 289 mg (total yield: 43%) of GDP-rhodeose in the form of a white powder.

$^1$H-NMR (D$_2$O, 250.134 MHz, ppm relative to D$_2$O: 4.8 ppm): 1.23 d, 7.6 Hz, 3H; 3.62 m, 3H; 3.75 q, 7.6 Hz, 1H; 4.20 m, 2H; 4.34 m, 1H; 4.52 m, 1H; 4.76 m, 1H; 4.91 t, 6.9 Hz, 1H; 5.93 d, 6.9 Hz, 1H; 8.05 s, 1H.

$^{31}$P-NMR (D$_2$O, 101.256 MHz): −10.89 ppm, d, 20.1 Hz; −12.72 ppm, d, 20.1 Hz.

What is claimed is:

1. A process for the preparation of nucleoside diphosphate or triphosphate sugars from protected nucleoside diphosphate or triphosphate sugars by complete removal of the hydroxyl protective groups of the formula —C(O)—R of the sugar residue, wherein R is linear or branched alkyl, unsubstituted phenyl or C$_1$–C$_4$alkyl- or C$_1$–C$_4$alkoxy-substituted phenyl, which process comprises removing the hydroxyl protective groups enzymatically with acetylesterase.

2. A process according to claim 1, wherein R is C$_1$–C$_8$alkyl.

3. A process according to claim 2, wherein R is C$_1$–C$_4$alkyl.

4. A process according to claim 1, wherein the sugar residue of the nucleoside diphosphate or triphosphate sugars is the residue of a sugar monomer or sugar dimer, and in the case of the sugar dimer the sugar monomers are linked to one another α or β-(anomeric center→n)glycosidically, n being a number from 1 to 9 and the term (anomeric center→n) indicating the positions of the glycosidic linkage of the two participating monomers.

5. A process according to claim 4, wherein the sugar monomer is selected from the group consisting of compounds whose structure conforms to the formula (CH$_2$O)$_m$, where m is a natural number from 3 to 9, as well as polyhydroxyaldehydes, polyhydroxyketones, polyhydroxyacids and polyhydroxyamines.

6. A process according to claim 5, wherein the sugar monomer is selected from the group consisting of D- and L-aldopyranoses and D- and L-aldofuranoses, of the group consisting of D- and L-ketopyranoses and D- and L-ketofuranoses or of the group consisting of D- and L-diketopyranoses.

7. A process according to claim 5, wherein the sugar monomer is selected from the group consisting of deoxy sugars of the D- and L-configuration, 2-, 3-, 4- and 6-deoxyamino sugars of the D- and L-configuration deoxyacylamino sugars, 2-, 3-, 4- and 6-deoxyhalogeno sugars, where halogen is F, Cl or Br, and 2-, 3-, 4- and 6deoxysulfhydryl sugars.

8. A process according to claim 7, wherein the sugar monomer is selected from the group consisting of 2-, 3-, 4- and 6-deoxyaldoses, 1,2-dideoxyaldoses 1-, 3-, 4- and 6-deoxyketoses 2-, 3-, 4- and 6-deoxyamino sugars of the D- and L-configuration, deoxyacylamino sugars, 2-, 3-, 4- and 6-deoxyhalogeno sugar, where halogen is F, Cl or Br, and 2-, 3-, 4- and 6-deoxysulfhydryl sugars.

9. A process according to claim 8, wherein the sugar is selected from the group consisting of fucose, rhamnose, digitoxose, glucal, galactal, fucal, glucosamine, mannosamine, galactosamine, fucosamine, N-acylglucosamine, N-acylmannosamine, N-acylgalactosamine and N-acylfucosamine.

10. A process according to claim 4, wherein the sugar monomer is arabinose, galactose, glucose, mannose, fucose, 2-fluorofucose, 2-aminofucose or rhodeose.

11. A process according to claim 1, wherein the nucleoside as part of the nucleoside diphosphate or triphosphate sugars is a natural or unnatural synthetic nucleoside.

12. A process according to claim 11, wherein the nucleoside is selected from the group consisting of guanosine, xanthosine, inosine, uridine, 2'-deoxy-2-aminoadenosine, 2'-deoxy-5-methylcytidine, 2'-deoxyadenosine, 2'-deoxycytidine, 2'-deoxyguanosine and thymidine.

13. A process according to claim 11, wherein the nucleoside is selected from the group consisting of guanosine, xanthosine, inosine and uridine.

14. A process according to claim 1, wherein the unprotected nucleoside diphosphate and triphosphate sugars are compounds of formula II

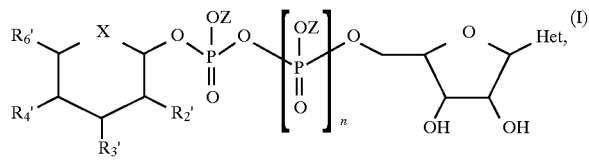

wherein

X is an oxygen, sulfur or carbon atom,

Z is Na, K, Li or Mg,

R$_{6'}$ is H or CH$_2$R$_{7'}$,

R$_{2'}$, R$_{3'}$, R$_4$, and R$_7$, are each independently of one another H, halogen, SH, NH$_2$, NHR or OH, R is linear or branched C$_1$–C$_8$alkyl, unsubstituted phenyl or C$_1$–C$_4$alkyl- or C$_1$–C$_4$alkoxy-substituted phenyl, and Het is a purine or pyrimidine base.

15. A process according to claim 1, wherein the protected nucleoside diphosphate and triphosphate sugars are compound of formula I

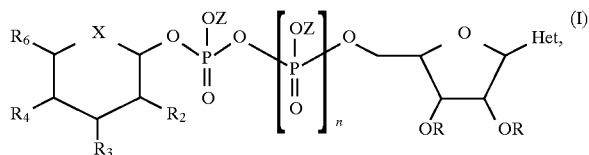

wherein n is 1 or 2,

X is an oxygen, sulfur or carbon atom,

Z is Na, K, Li or Mg, $R_6$ is H or $CH_2R_7$, $R_2$, $R_3$, $R_4$ and $R_7$ are each independently of one another H, halogen, SH, $NH_2$, NHR, or a radical —O—C(O)—R, R is linear or branched $C_1$–$C_8$alkyl, unsubstituted phenyl or $C_1$–$C_4$alkyl- or $C_1$–$C_4$alkoxy-substituted phenyl, and Het is purine or pyrimidine base, with the proviso that either at least one of $R_2$, $R_3$ and $R_4$ is a radical —O—C(O)—R or $R_6$ is $CH_2$—O—C(O)—R.

16. A process according to claim 15, wherein X is an oxygen or carbon atom, Z is Na, K, Li or Mg, $R_2$, $R_3$, $R_4$ and $R_6$ are each independently of one another a —OC(O)—R radical, R is linear or branched $C_1$–$C_4$akyl or phenyl, and Het is a purine or pyrimidine base.

17. A process according to claim 16, wherein X is an oxygen atom, Z is Na, $R_2$, $R_3$, $R_4$ and $R_6$ are each independently of one another a —OC(O)—R radical, R is linear or branched $C_1$–$C_4$akyl or phenyl, and Het is a purine or pyrimidine base.

18. A process according to claim 17, wherein R is methyl, ethyl, i- or n-propyl.

19. A process according to claim 1, wherein nucleoside diphosphate and triphosphate sugars are used which are protected in the sugar residue and whose protective groups are identical.

20. A process according to claim 1, wherein the nucleoside diphosphate and triphosphate sugars are guanosine diphosphate fucose, xanthosine diphosphate fucose, inosine diphosphate fucose, guanosine diphosphate-2-fluorofucose, guanosine diphosphate-β-L-2-aminofucose, guanosine triphosphate fucose, guanosine diphosphate-D-arabinose, guanosine diphosphate-β-L-galactose, uridine diphosphate galactose, guanosine diphosphate-β-L-glucose, guanosine diphosphate-α-D-mannose and guanosine diphosphate-β-D-rhodeose.

21. A process according to claim 1, wherein the enzymatic removal is carried out with soluble or immobilised enzyme.

22. A compound prepared by the process of claim 1 selected from the group consisting of xanthosine diphosphate fucose, inosine diphosphate fucose, guanosine diphosphate-2- fluorofucose, guanosine diphosphate-β-L-2-aminofucose, guanosine triphosphate fucose, guanosine diphosphate-D-arabinose, and guanosine diphosphate-β-D-rhodeose.

23. A process for the preparation of nucleoside diphosphate or triphosphate sugars from protected nucleoside diphosphate or triphosphate sugars by complete removal of the hydroxyl protective groups of the formula —C(O)—R of the sugar residue, wherein R is linear or branched alkyl, unsubstituted phenyl or $C_1$–$C_4$alkyl or $C_1$–$C_4$alkoxy-substituted phenyl, which process comprises carrying out the removal enzymatically with acetylesterase in the absence of buffers.

24. A process for the preparation of nucleoside diphosphate or triphosphate sugars, wherein a protected sugar-1-phosphate is reacted with a nucleoside monophosphate or diphosphate, which process comprises activating either the sugar-1-phosphate or the corresponding nucleoside prior to coupling it with a carbonyl bisazole and, after coupling has been carried out, removing the protective groups enzymatically with acetylesterase.

25. A process according to claim 24, wherein the carbonyl diimidazole, carbonyl ditriazole, thiocarbonyl diimidazole or carbonyl dioxydibenzotriazole.

* * * * *

UNITED STATES PATENT AND TRADEMARK OFFICE
CERTIFICATE OF CORRECTION

PATENT NO. : 5,888,777  
DATED : March 30, 1999  
INVENTOR(S) : Reinhold Oehrlein, et. al.

Page 1 of 2

It is certified that error appears in the above-identified patent and that said Letters Patent is hereby corrected as shown below:

Column 4, the formula in lines 8-14, should read:

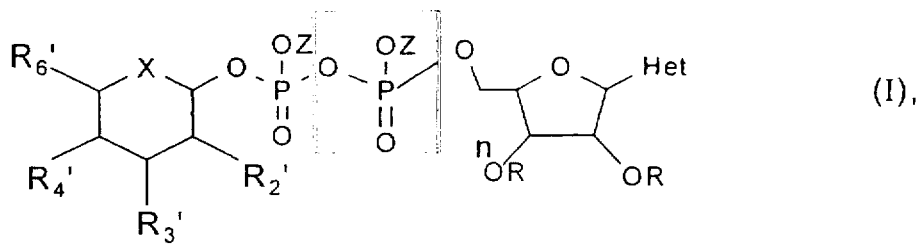 (I),

Column 4, the formula in lines 28-34, should read:

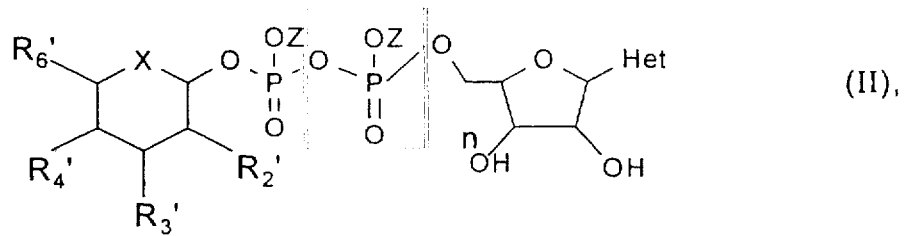 (II),

Column 14, claim 14, lines 4-9, the formula should read:

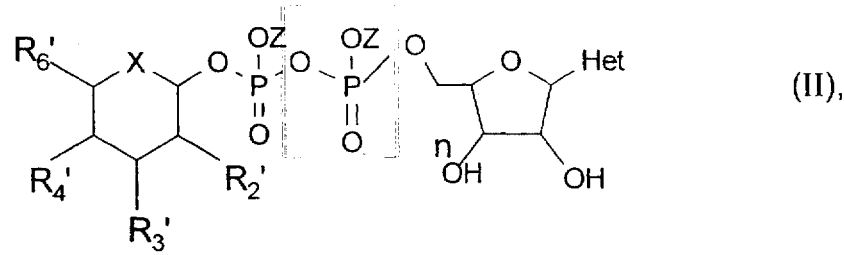 (II),

UNITED STATES PATENT AND TRADEMARK OFFICE
CERTIFICATE OF CORRECTION

PATENT NO. : 5,888,777
DATED : March 30, 1999
INVENTOR(S) : Reinhold Oehrlein, et. al.

It is certified that error appears in the above-identified patent and that said Letters Patent is hereby corrected as shown below:

Column 14, claim 15, lines 4-9, the formula should read:

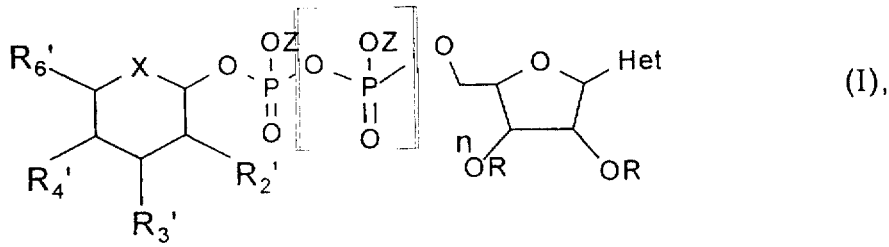

(I),

Column 15, line 4 of claim 16, "akyl" should read:

-- alkyl --.

Column 15, line 4 of claim 17, "akyl" should read:

-- alkyl --.

Column 16, line 2 of claim 24, after sugars, insert

-- protected in the sugar residue --

Signed and Sealed this

Seventh Day of March, 2000

Attest:

Q. TODD DICKINSON

Attesting Officer

Commissioner of Patents and Trademarks